United States Patent
Yoshii et al.

(10) Patent No.: US 10,271,913 B2
(45) Date of Patent: Apr. 30, 2019

(54) SURGICAL TOOL

(71) Applicant: OLYMPUS CORPORATION, Tokyo (JP)

(72) Inventors: Toshihiro Yoshii, Tokyo (JP); Shuya Jogasaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 258 days.

(21) Appl. No.: 15/086,707

(22) Filed: Mar. 31, 2016

(65) Prior Publication Data

US 2016/0206390 A1     Jul. 21, 2016

Related U.S. Application Data

(63) Continuation of application No. PCT/JP2014/081550, filed on Nov. 28, 2014.

(30) Foreign Application Priority Data

Nov. 29, 2013 (JP) .................................. 2013-248642

(51) Int. Cl.
    *A61B 34/00*     (2016.01)
    *A61B 17/29*     (2006.01)
    (Continued)

(52) U.S. Cl.
    CPC .............. *A61B 34/71* (2016.02); *A61B 34/30* (2016.02); *A61B 34/37* (2016.02); *F16H 19/005* (2013.01);
    (Continued)

(58) Field of Classification Search
    CPC . A61B 1/00147; A61B 1/0016; A61B 1/0057; A61B 17/00234; A61B 17/28;
    (Continued)

(56) References Cited

U.S. PATENT DOCUMENTS

| | | | | |
|---|---|---|---|---|
| 4,500,780 A | * | 2/1985 | Buan | ..................... G01D 5/3473 250/231.13 |
| 7,285,088 B2 | * | 10/2007 | Miyake | ................ A61B 1/0052 600/146 |

(Continued)

FOREIGN PATENT DOCUMENTS

| EP | 1908390 A1 | 4/2008 |
|---|---|---|
| JP | H06-130307 A | 5/1994 |

(Continued)

OTHER PUBLICATIONS

International Search Report dated Feb. 3, 2015 issued in PCT/JP2014/081550.

(Continued)

*Primary Examiner* — Ryan J. Severson
(74) *Attorney, Agent, or Firm* — Scully, Scott, Murphy & Presser, P.C.

(57) ABSTRACT

A surgical tool includes: a treatment section that treats an object to be treated; a power source that generates a power to operate the treatment section; a traction section connected to the treatment section and the power source; a switching section that switches a transmission state of the power from the power source to the traction section between a state in which the power can be transmitted and a state in which the power cannot be transmitted; and a tension-applying section that has a pulley and applies a predetermined initial tension to the traction section by applying a power to the pulley in the state in which the power cannot be transmitted, wherein the traction section is hung on the pulley via the power source from the treatment section and is connected to the treatment section via the power source.

10 Claims, 9 Drawing Sheets

(51) Int. Cl.
*F16H 19/06* (2006.01)
*F16H 19/00* (2006.01)
*A61B 34/30* (2016.01)
*A61B 34/37* (2016.01)
*F16H 19/04* (2006.01)

(52) U.S. Cl.
CPC ......... *F16H 19/04* (2013.01); *F16H 19/0672* (2013.01); *A61B 17/29* (2013.01); *A61B 2034/715* (2016.02); *F16H 2019/0695* (2013.01)

(58) Field of Classification Search
CPC ................ A61B 17/2804; A61B 17/29; A61B 2017/00292; A61B 2017/003; A61B 2017/00318; A61B 2017/00323; A61B 2017/00327; A61B 2017/2901; A61B 2017/2902; A61B 2017/2908; A61B 2017/2927; A61B 2017/2932; A61B 2034/302; A61B 2034/305; A61B 2034/715; A61B 34/30; A61B 34/37; A61B 34/71; A61B 34/72
See application file for complete search history.

(56) References Cited

U.S. PATENT DOCUMENTS

| | | | | |
|---|---|---|---|---|
| 7,540,867 B2* | 6/2009 | Jinno | ................... | A61B 34/70 414/7 |
| 8,277,443 B2* | 10/2012 | Jinno | ................... | B25J 9/104 606/1 |
| 8,333,780 B1* | 12/2012 | Pedros | ................... | A61B 17/29 600/37 |
| 8,382,659 B2* | 2/2013 | Ashida | ................ | A61B 1/00006 600/145 |
| 8,644,988 B2* | 2/2014 | Prisco | ................... | A61B 34/71 600/146 |
| 8,647,330 B2* | 2/2014 | Iida | ...................... | A61B 34/71 606/1 |
| 8,795,324 B2* | 8/2014 | Kawai | ................... | A61B 17/29 606/205 |
| 9,101,379 B2* | 8/2015 | Au | ..................... | A61B 19/2203 |
| 9,198,729 B2* | 12/2015 | Rogers | ............... | A61B 19/2203 |
| 9,259,274 B2* | 2/2016 | Prisco | ................... | B25J 9/1045 |
| 9,770,299 B2* | 9/2017 | Komuro | ................ | A61B 90/50 |
| 9,775,677 B2* | 10/2017 | Hyodo | ................... | A61B 34/71 |
| 2005/0054899 A1* | 3/2005 | Miyake | ................ | A61B 1/0052 600/152 |
| 2009/0031842 A1* | 2/2009 | Kawai | ................... | A61B 17/29 74/490.01 |
| 2009/0112230 A1* | 4/2009 | Jinno | ...................... | B25J 9/104 606/130 |
| 2010/0082041 A1* | 4/2010 | Prisco | ................... | B25J 9/1045 606/130 |
| 2010/0241135 A1* | 9/2010 | Iida | ........................ | A61B 34/71 606/130 |
| 2011/0009698 A1* | 1/2011 | Ashida | ............... | A61B 1/00006 600/118 |
| 2012/0123200 A1* | 5/2012 | Rogers | ............... | A61B 19/2203 600/104 |
| 2012/0123441 A1* | 5/2012 | Au | ..................... | A61B 19/2203 606/130 |
| 2014/0107667 A1* | 4/2014 | Komuro | ................. | A61B 19/22 606/130 |
| 2014/0249545 A1* | 9/2014 | Hyodo | ............... | A61B 19/2203 606/130 |
| 2016/0038239 A1* | 2/2016 | Yamanaka | ......... | A61B 19/2203 606/130 |
| 2016/0051331 A1* | 2/2016 | Rogers | ............... | A61B 19/2203 606/130 |
| 2016/0166342 A1* | 6/2016 | Prisco | ................... | B25J 9/1045 606/130 |
| 2016/0206390 A1* | 7/2016 | Yoshii | ................. | F16H 19/0672 |
| 2016/0213438 A1* | 7/2016 | Jogasaki | ............... | A61B 1/0016 |
| 2017/0251902 A1* | 9/2017 | Jogasaki | ............ | A61B 1/00133 |
| 2017/0325905 A1* | 11/2017 | Jogasaki | ................ | A61B 34/74 |
| 2017/0333143 A1* | 11/2017 | Yoshii | .................... | A61B 34/30 |
| 2017/0340398 A1* | 11/2017 | Higuchi | ................. | A61B 34/37 |

FOREIGN PATENT DOCUMENTS

| | | |
|---|---|---|
| JP | H07-116104 A | 5/1995 |
| JP | H10-174686 A | 6/1998 |
| JP | 2004-350866 A | 12/2004 |
| JP | 2007-029167 A | 2/2007 |
| JP | 2009-225992 A | 10/2009 |
| JP | 2012-504016 A | 2/2012 |
| JP | 2013-103074 A | 5/2013 |
| WO | WO 2010/039387 A1 | 4/2010 |
| WO | WO 2012/064528 A1 | 5/2012 |
| WO | 2013/002414 A1 | 1/2013 |
| WO | WO 2013/073713 A1 | 5/2013 |

OTHER PUBLICATIONS

Extended Supplementary European Search Report dated Jun. 9, 2017 in European Patent Application No. 14 86 6697.7.

* cited by examiner

SURGICAL TOOL

CROSS REFERENCE TO RELATED APPLICATIONS

This application is a continuation application based on a PCT Patent Application No. PCT/JP2014/081550, filed on Nov. 28, 2014, whose priority is claimed on Japanese Patent Application No. 2013-248642, filed Nov. 29, 2013, the entire content of which are hereby incorporated by reference.

BACKGROUND OF THE INVENTION

Field of the Invention

The present invention relates to a medical surgical tool.

Description of the Related Art

In the related art, medical manipulators for assisting in surgery are known. For example, Japanese Unexamined Patent Application, First Publication No. H10-174686 (hereinafter referred to as Patent Document 1) discloses that loosening of a wire is prevented by a spring being interposed in an intermediate part of the wire in a mechanism that transmits the power output from a drive motor via the wire. Moreover, Patent Document 1 discloses that a pulley on a driven side is positioned by a minute vibration generating device that transmits minute vibration to the pulley on the driven side on which the wire is hung.

Additionally, for example, United States patent application, Publication No. 2010/0082041 (hereinafter referred to as Patent Document 2) discloses a surgical tool for surgery. The surgical tool described in Patent Document 2 includes an end effector provided at a distal end of a shaft, a tendon member connected to the end effector and inserted through the shaft, and a winding-up device that tractions the tendon member provided at a proximal end of the shaft. Moreover, the surgical tool described in Patent Document 2 includes a preloading system for applying initial tension to the tendon member.

SUMMARY

According to a first aspect of the present invention, a surgical tool includes: a treatment section that treats an object to be treated; a power source that generates a power to operate the treatment section; a traction section connected to the treatment section and the power source; a switching section that switches a transmission state of the power from the power source to the traction section between a state in which the power can be transmitted and a state in which the power cannot be transmitted; and a tension-applying section that has a pulley and applies a predetermined initial tension to the traction section by applying a power to the pulley in the state in which the power cannot be transmitted, wherein the traction section is hung on the pulley via the power source from the treatment section and is connected to the treatment section via the power source.

According to a second aspect of the present invention, in the surgical tool according to the first aspect, the traction section may be slidably hung on the pulley.

According to a third aspect of the present invention, in the surgical tool according to the first or second aspect, the switching section may include: a driver connected to the power source; and a movable body that is connected to the traction section, is attachable to and detachable from the driver, and is engaged with the driver and thereby moved by the driver.

According to a fourth aspect of the present invention, in the surgical tool according to the third aspect, the driver may be a pinion connected to the power source, and the movable body may be an internal gear having an outer peripheral surface frictionally engageable with the traction section and an inner peripheral surface having gear teeth meshing with the pinion and is attachable to and detachable from the pinion.

According to a fifth aspect of the present invention, in the surgical tool according to the third aspect, the driver may be a pinion connected to the power source, the movable body may be a rack coupled to the traction section, and the switching section may further include a movable part that moves the pinion with respect to the rack in order to attach and detach the pinion to and from the rack.

DETAILED DESCRIPTION OF THE PREFERRED EMBODIMENTS

First Embodiment

A first embodiment of a surgical tool of the invention will be described.

The surgical tool of the present embodiment is incorporated into a medical manipulator system for performing a medical procedure.

First, the configuration of the medical manipulator system into which the surgical tool of the present embodiment is incorporated will be described.

Figure 1:
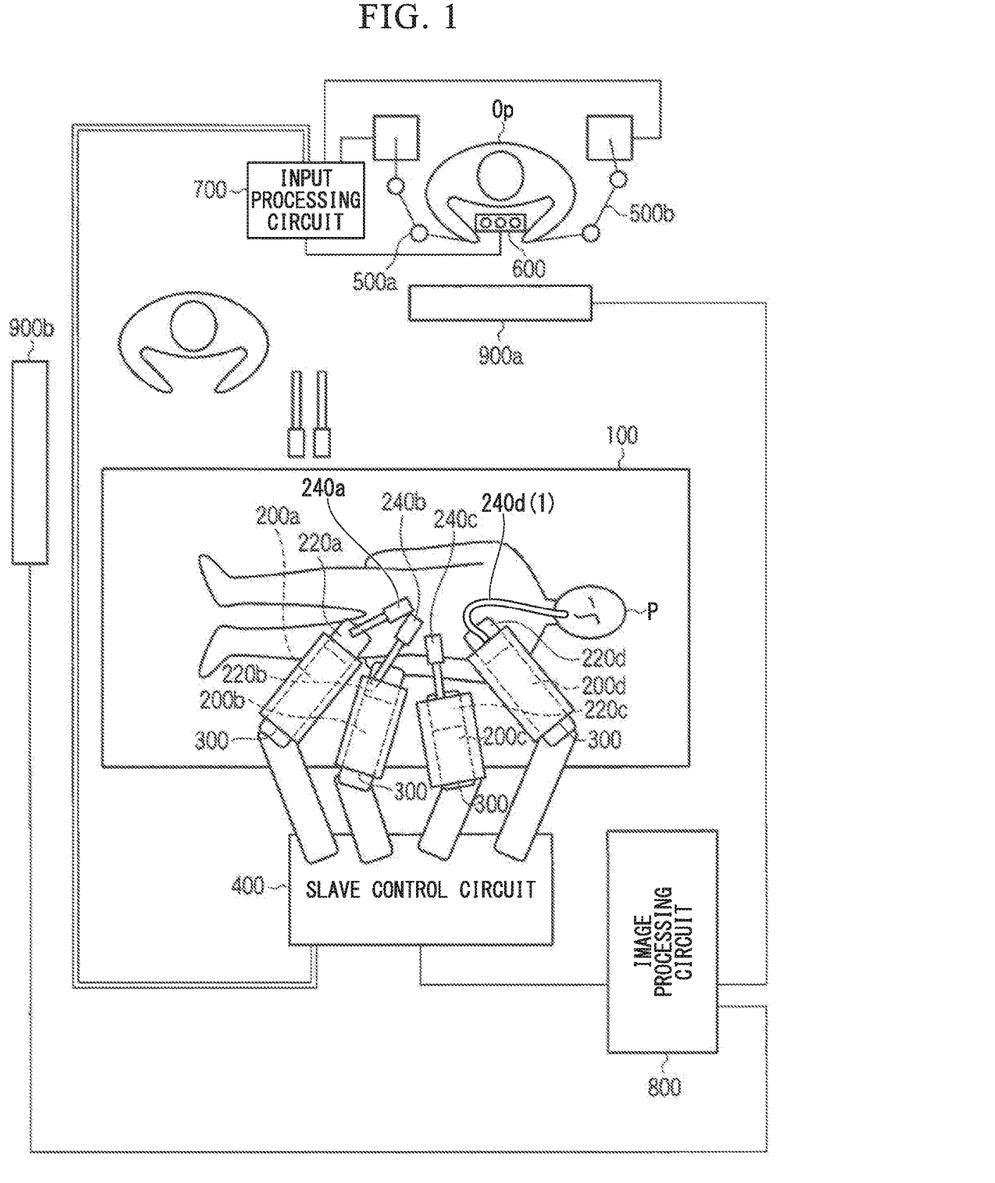
FIG. 1 is a schematic view illustrating an example of the configuration of a medical manipulator system to which a surgical tool of a first embodiment of the invention is applicable.

FIG. 1 is a schematic view illustrating an example of the configuration of the medical manipulator system to which the surgical tool of the invention is applied.

An example of a master slave type medical manipulator system is illustrated in FIG. 1. The master slave type medical manipulator system is a system that has two types of arms consisting of a master arm and a slave arm and that remotely controls the slave arm so as to follow the operation of the master arm. In the present embodiment, a surgical tool 1 is mountable on the slave arm.

The medical manipulator system shown in FIG. 1 has a surgical bed 100, slave arms 200a, 200b, 200c, and 200d, a slave control circuit 400, master arms 500a and 500b, an operating unit 600, an input processing circuit 700, an image processing circuit 800, an operator display 900a, and an assistant display 900b.

Hereinafter, in order to simplify description, symbols "Xa, Xb, . . . , Xz" in alphabetical order may be expressed like "Xa to Xz". For example, the "slave arms 200a, 200b, 200c, and 200d" may be expressed as the "slave arms 200a to 200d".

The surgical bed 100 is a bed on which a patient P who is a target to be observed and treated is placed. The plurality of slave arms 200a to 200d are installed in the vicinity of the surgical bed 100. In addition, the slave arms 200a to 200d may be installed at the surgical bed 100.

The respective slave arms 200a to 200d are configured to have a plurality of multiple degree-of-freedom joints, respectively, and the surgical tool 1, the surgical tools 240a to 240d, or the like mounted on distal end sides (referred to as sides directed to a body cavity of a patient P) of the slave arms 200a to 200d are positioned with respect to the patient P placed on the surgical bed 100 by bending the respective multiple degree-of-freedom joints. Each multiple degree-of-freedom joint is individually driven by a power unit (not illustrated). As the power unit, for example, a motor having a servo mechanism including an incremental encoder, a speed reducer, or the like, can be used, and the operation control of the motor is performed by the slave control circuit 400.

The surgical tool 1 and the other surgical tools 240a to 240d may be rigid or may be flexible. That is, as the surgical tool 1 and the other surgical tools 240a to 240d, a surgical tool that operates an effector for performing a treatment on a living body by the push and pull of a rigid rod, and a surgical tool that operates an effector for performing a treatment on a living body by the traction of flexible wires can be appropriately selected and adopted. In addition, even when the surgical tool 1 and the other surgical tools 240a to 240d are rigid, a configuration in which the effectors are operated by the traction of the flexible wires may be provided. In the present embodiment, the surgical tool 1 has a configuration in which a driving force for operating an effector is transmitted to an effector through a flexible wire.

An example in which the surgical tool 1 and the other surgical tools 240a to 240c are rigid and the surgical tool 240d is flexible is illustrated in FIG. 1. The flexible surgical tool 240d is introduced from a natural opening of a patient, such as the mouth, via the alimentary canal or the like to the inside of the body.

The slave control circuit 400 is configured to have, for example, a CPU, a memory, and the like. The slave control circuit 400 stores a predetermined program for performing the control of the slave arms 200a to 200d, and controls the operation of the slave arms 200a to 200d or the surgical tool 1 and the other surgical tools 240a to 240d according to control signals from the input processing circuit 700. That is, the slave control circuit 400 specifies a slave arm (or the surgical tool 1), which is an operation target of a master arm operated by an operator Op, on the basis of a control signal from the input processing circuit 700, and calculates a driving amount required in order to cause the specified slave arm or the like to perform a movement corresponding to the operation amount of the master arm by the operator Op.

Also, the slave control circuit 400 controls the operation of a slave arm or the like that is the operation target of a master arm according to the calculated driving amount. In this case, the slave control circuit 400 inputs a driving signal to a corresponding slave arm, and controls the magnitude and polarity of the driving signal according to a detection signal input from a position detector of a power unit according to the operation of the corresponding slave arm so that the driving amount of the slave arm that is an operation target becomes a target driving amount.

The master arms 500a and 500b are constituted by a plurality of link mechanisms. Respective links that constitute the link mechanisms are provided with, for example, position detectors, such as incremental encoders. By detecting the operation of the respective links with the position detectors, the operation amounts of the master arms 500a and 500b are detected in the input processing circuit 700.

The medical manipulator system of FIG. 1 operates the four slave arms using the two master arms 500a and 500b, and needs to appropriately switch the slave arms that are operation targets of the master arms. Such switching is performed, for example, by the operation of the operating unit 600 by the operator Op. Of course, if the operation targets have one-to-one correspondence by causing the number of the master arms and the number of the slave arms to be the same number, such switching is unnecessary.

The operating unit 600 has various operating members, such as switching buttons for switching the slave arms that are the operation targets of the master arms 500a and 500b, a scaling changing switch that changes the operation ratio of the masters and the slaves, and a foot switch for emergency-stopping the system. When a certain operating member constituting the operating unit 600 is operated by the operator Op, an operation signal according to the operation of the corresponding operating member is input from the operating unit 600 to the input processing circuit 700.

The input processing circuit 700 analyzes operation signals from the master arms 500a and 500b and operation signals from the operating unit 600, and generates control signals for controlling the medical manipulator system according to analysis results of the operation signals to input the control signals to the slave control circuit 400.

The image processing circuit 800 performs various kinds of image processing for displaying image signals input from the slave control circuit 400, to generate display image data in the operator display 900a and the assistant display 900b. The operator display 900a and the assistant display 900b are constituted by, for example, liquid crystal displays, and display images based on the image data generated in the image processing circuit 800 according to image signals acquired via an observation instrument.

In the medical manipulator system configured as described above, if the operator Op operates the master arms 500a and 500b, the corresponding slave arms and the surgical tool 1 and the other surgical tools 240a to 240d attached to the slave arms operate in correspondence with the movement of the master arms 500a and 500b. Accordingly, a desired procedure can be performed on the patient P.

In addition, in FIG. 1, reference signs 220a, 220b, 220c, and 220d designate surgical power transmission adapters, which are interposed between the slave arms 200a, 200b, 200c, and 200d, and the surgical tools 240a, 240b, 240c, and 240d to connect the slave arms 200a, 200b, 200c, and 200d and the surgical tools 240a, 240b, 240c, and 240d, respectively.

Additionally, reference signs 300 designate drapes for dividing a part (clean region) where sterilization processing is performed in the medical manipulator system related to the present embodiment, and a part (unclean region) where sterilization processing is not performed.

Next, the surgical tool 1 incorporated into the medical manipulator system of the present embodiment will be described. In addition, in the description of the surgical tool 1 of the present embodiment, a side directed to the body cavity of the patient P in a state in which the surgical tool 1 is incorporated into the medical manipulator system is a distal side of the surgical tool 1, and a connection portion side, which is a side away separated from the patient P in the surgical tool 1 and is connected to the a medical manipulator system, is a proximal side of the surgical tool 1.

Figure 2:
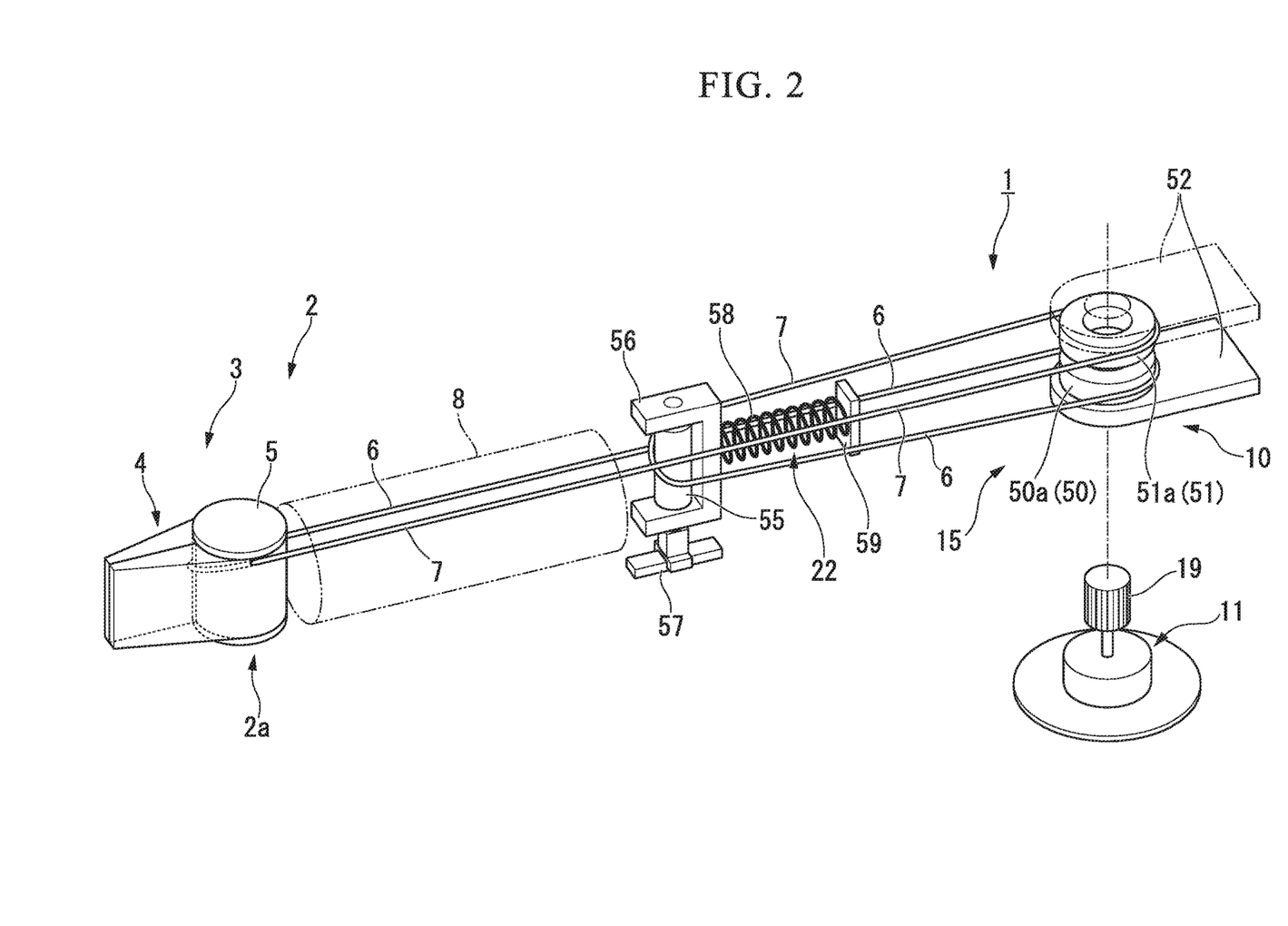
FIG. 2 is a perspective view illustrating the internal structure of the surgical tool of the embodiment.
Figure 3:
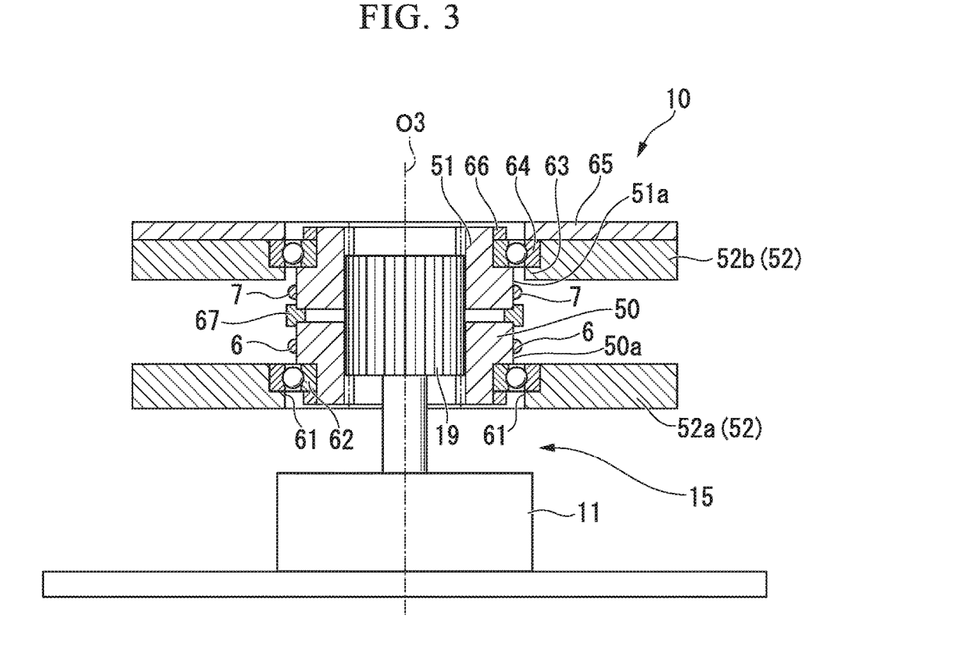
FIG. 3 is a schematic view illustrating the configuration of a driving unit in the surgical tool.

FIG. 2 is a perspective view illustrating the internal structure of the surgical tool 1. FIG. 3 is a schematic view illustrating the configuration of a driving unit of the surgical tool 1.

The surgical tool 1 of the present embodiment is a flexible surgical tool that is attached to the slave arm 200*d* illustrated in FIG. 1. The surgical tool 1 operates to correspond to operations that are input to master arms 500*a* and 500*b*.

As illustrated in FIG. 2, the surgical tool 1 has an insertion unit 2 that has a distal end part 2*a* inserted into the inside of a body, and a driving unit 10 that is attached to a proximal end of the insertion unit 2.

The insertion unit 2 has a treatment section 3 for treating an object to be treated, and a pipe part 8 that has the treatment section 3 coupled to a distal end thereof.

Additionally, the surgical tool 1 may have a function as an endoscope. That is, the surgical tool 1 may be an endoscope. When the surgical tool 1 is an endoscope, the surgical tool 1 includes observation means for observing (treating) the inside of a body as the treatment section 3. Additionally, the surgical tool 1 when being constituted as an endoscope may further include illumination means for radiating illumination light to an object to be observed or an object to be treated. Additionally, although the surgical tool 1 includes the means for observing the inside of a body, means for performing surgical treatment may not be included.

The treatment section 3 is provided at the distal end part of the insertion unit 2. The treatment section 3 may include a well-known configuration corresponding to the contents of treatment for an object to be treated. For example, examples of the treatment section 3 may include forceps, a knife, a marking device, a suture device, and the like. In the present embodiment, the treatment section 3 corresponds to grasping forceps 4 that grip an object to be treated.

The grasping forceps 4 are openable and closable by a well-known opening and closing mechanism, and are swingable by a turning operation having a predetermined turning shaft 5 as a turning center. In addition, as another mechanism for swinging the grasping forceps 4, a mechanism in which a plurality of bending pieces that are bendably coupled together are provided at the distal end of the insertion unit 2, and modification in a curved shape is possible as a whole as the respective bending pieces make bending movements is known.

Respective distal portions of a flexible first traction member 6 (first traction part) and a flexible second traction member 7 (second traction part) are wound around an outer peripheral surface of the turning shaft 5. Distal ends of the first traction member 6 and the second traction member 7 are connected to the turning shaft 5. In the present embodiment, the first traction member 6 and the second traction member 7 are connected together at base ends thereof. That is, the first traction members 6 and the second traction members 7 are a series of linear members.

In addition, when a swinging mechanism in which the above bending pieces are used is adopted, the distal ends of the first traction member 6 and the second traction member 7 are fixed to a bending piece located nearest to the distal end among the plurality of bending pieces, and structures (for example, a proximal end of the treatment section 3, or the like) that are at positions nearer to the distal end than the bending piece located nearest to the distal end.

The first traction member 6 and the second traction member 7 have flexibility such that the members can be bent along the outer peripheral surface of the turning shaft 5. For example, the first traction member 6 and the second traction member 7 are formed in the shape of a wire, using stainless steel (for example, SUS304) as a material.

In the present embodiment, the first traction member 6 and the second traction member 7 are wound around the outer peripheral surface of the turning shaft 5, and are tractioned for swinging. For this reason, it is preferable that the materials of the first traction member 6 and the second traction member 7 are apt to bend and do not easily expand and contract. However, generally, materials that are apt to bend tend to expand and contract, and materials that are not apt to expand and contract do not easily bend. In the present embodiment, the materials of the first traction member 6 and the second traction member 7 are selected paying attention to the balance between the easiness of bending and retractility in the first traction member 6 and the second traction member 7.

The pipe part 8 is a hollow member that has a holding part 9 that turnably holds the turning shaft 5 at a distal end thereof.

The first traction member 6 and the second traction member 7 are inserted through the inside of the pipe part 8 so as to be capable of being advanced and retracted. In the present embodiment, the pipe part 8 is rigid and has a cylindrical shape. In addition, the pipe part 8 may have flexibility.

The driving unit 10 has a power source 11 that generates power for swinging the treatment section 3 illustrated in FIG. 2, a switching section 15 that switches a state in which power is transmitted from the power source 11 to the first traction member 6 and the second traction member 7, and a tension-applying section 22 that applies tension to the first traction member 6 and the second traction member 7.

The power source 11 has a turning shaft that is capable of rotationally operating. In the present embodiment, the power source 11 is a servo motor that turns the turning shaft under the supply of electric power. A pinion 19 (driver), which is capable of meshing with internal gears 50 and 51 (to be described below) that are portions of the switching section 15, is fixed to the turning shaft of the power source 11.

In the present embodiment, the internal gears 50 and 51 are manually attachable to and detachable from the pinion 19 of the power source 11. That is, in the present embodiment, the switching section 15 is constituted by the internal gears 50 and 51 and the pinion 19.

The switching section 15 is provided with the first internal gear 50 that has an outer peripheral surface 50*a* frictionally engaged with the first traction member 6 and serves as a first movable body, and the second internal gear 51 that has an outer peripheral surface 51*a* frictionally engaged with the second traction member 7 and serves as a second movable body.

In addition, although the embodiment concerned is an aspect in which the first traction member 6 is frictionally engaged with the outer peripheral surface 50a of the first internal gear 50 and the second traction member 7 is frictionally engaged with the outer peripheral surface 51a of the second internal gear 51, for example, the engagement may be made by means other than the frictional engagement, such as crimping or bonding the first traction member 6 to the outer peripheral surface 50a. Moreover, if the first traction member 6 is wound around the outer peripheral surface 50a several times, the amount of stroke of the turning shaft 5 can also be gained. The same applies to the relationship between the second traction member 7 and the outer peripheral surface 51a.

Additionally, the first traction member 6 and the second traction member 7 are all coupled to the tension-applying section 22.

The tension-applying section 22 connects the first traction member 6 and the second traction member 7 between the treatment section 3 and the power source 11. The tension-applying section 22 includes a pulley 55 that has a linear member serving as the first traction member 6 and the second traction member 7 hung on an outer peripheral surface thereof, a pulley holding part 56 that turnably holds the pulley 55, a guide 57 that slidably holds the pulley holding part 56 in a direction in which a distal end and a proximal end in the driving unit 10 are mutually connected, and a spring 58 for pressing the pulley holding part 56 toward a distal side.

The spring 58 moves the pulley holding part 56 along the guide 57 and holds the pulley holding part 56 at a position where constant tension is applied to the linear member constituting the first traction member 6 and the second traction member 7 so that constant tension is applied to the linear member constituting the first traction member 6 and the second traction member 7. A proximal end of the spring 58 is fixed to a support part 59 disposed on the proximal side of the pulley 55.

As illustrated in FIG. 3, the first internal gear 50 and the second internal gear 51 are independently rotatable with the same rotation center O3 as a center, and are capable of meshing with the pinion 19, respectively. Specifically, the switching section 15 has a gear case 52 in which both of the first internal gear 50 and the second internal gear 51 are housed.

The gear case 52 has a first support part 61 coupled to the first internal gear 50 via a bearing 62, a second support part 63 coupled to the second internal gear 51 via a bearing 64, and a first holding member 65 and a second holding member 66 for holding the bearing 64.

The positional relationship between the first support part 61 and the second support part 63 is brought into a fixed state, in a state a gap is formed by a washer 67 so that the first internal gear 50 and the second internal gear 51 are housed between the first support part 61 and the second support part 63. The gear case 52 forms a holding part that holds the first internal gear 50 and the second internal gear 51 so that the first internal gear 50 and the second internal gear 51 are rotatable independently from each other with the same rotation center as a center.

In the present embodiment, the bearing 62 and the bearing 64 consist of ball bearings.

A ring on an outer peripheral side of the bearing 62 is fitted to the first support part 61. A ring on an inner peripheral side of the bearing 62 is fitted to the first internal gear 50 by screw meshing.

A ring on an outer peripheral side of the bearing 64 is fitted to the second support part 63 and is covered with the first holding member 65. The first holding member 65 is fixed to the second support part 63. A ring on an inner peripheral side of the bearing 64 is fitted to the second internal gear 51 and is covered with the second holding member 66.

The second holding member 66 is fitted to the second internal gear 51 by screw meshing.

The first internal gear 50 and the second internal gear 51 are held by the gear case 52 via ball bearings (the bearings 62 and 64). For this reason, the sliding resistance when the first internal gear 50 and the second internal gear 51 are rotationally operated is small. Additionally, in the present embodiment, the first internal gear 50 and the second internal gear 51 can be easily incorporated into the gear case 52 by covering the first internal gear 50 and the second internal gear 51, with the first holding member 65 after the first and second internal gears are housed within the gear case 52 in a state in which the bearings 62 and 64 are fitted and the washer 67 is interposed.

In the present embodiment, a state in which both of the first internal gear 50 and the second internal gear 51 mesh with the pinion 19 and a state in which both of the first internal gear 50 and second internal gear 51 are separated from the pinion 19 are exclusively selected by the attachment and detachment operation of the first internal gear 50 and the second internal gear 51 to and from the pinion 19.

The operation of the surgical tool 1 of the present embodiment will be described.

The surgical tool 1 of the present embodiment is fixed to a slave arm, and the power source 11 of the driving unit 10 operates according to operation input to a master arm.

In the surgical tool 1, since the insertion unit 2 has the distal end part 2a inserted into the inside of a body, the insertion unit is sterilized before use. In contrast, the driving unit 10 does not have a portion inserted into the inside of a body, and it is sufficient if only the driving unit is covered with a sterilized drape. In the present embodiment, since neither an electronic apparatus nor a circuit is disposed in the insertion unit 2, the insertion unit 2 can cope with various kinds of sterilization, such as high-pressure steam sterilization and sterilization using ethylene oxide gas or the like.

In the surgical tool 1, since the insertion unit 2 is connected to the driving unit 10, the pinion 19 is brought into a state in which the pinion meshes with both of the first internal gear 50 and the second internal gear 51. In this state, if the turning shaft of the power source 11 is turned, the power output from the power source 11 is transmitted from the pinion turned together with the turning shaft to both of the first internal gear 50 and the second internal gear 51.

When the insertion unit 2 is deformed so that the insertion unit 2 is brought into a bent state in a state in which both of the first internal gear 50 and the second internal gear 51 mesh with the pinion 19, the path lengths of the first traction member 6 and the second traction member 7 may change, and thereby, "loosening" or "tightening" may occur in the first traction member 6 and the second traction member 7. In this case, the initial tension transmitted from the first traction member 6 and the second traction member 7 to the treatment section 3 may be out of a proper magnitude.

In the surgical tool 1 of the present embodiment, in a process in which the insertion unit 2 may be deformed into a complicated curved shape, such as a process in which the treatment section 3 is guided to an object region to be treated, both of the first internal gear 50 and the second internal gear 51 are brought into a state in which the first and second internal gears are separated from the pinion 19. Accordingly, when a tension that leads to loosening or tightening has occurred in the first traction member 6 and the second traction member 7, the first internal gear 50 and the second internal gear 51 rotate freely and reduces the tension change. Moreover, the tension applied to the first traction member 6 and the second traction member 7 by the tension-applying section 22 is substantially constantly maintained without being changed from the initial tension.

For example, after the treatment section 3 is appropriately guided to an object region to be treated, the first internal gear 50 and the second internal gear 51 are able to rotationally operate with the power from the power source 11, for example, by the coupling of the first internal gear 50 and the second internal gear 51 to the pinion 19 accompanying the operation of attaching the insertion unit 2 to the driving unit 10.

As described above, the surgical tool 1 of the present embodiment is a compact surgical tool that can keep initial tension constant as compared to the related-art structure in which a power source, a clutch, or the like is frequently used in order to adjust tension.

Additionally, the first traction member 6 and the second traction member 7 fixed to the turning shaft 5 of the treatment section 3 are hung on the outer peripheral surface of the pulley 55 constituting the tension-applying section 22, that is, the first traction member 6 and the second traction member 7 are slidably hung on the pulley 55. Therefore, the treatment section 3 freely moves in a state in which the pinion 19 is separated from the first internal gear 50 and the second internal gear 51 and power cannot be transmitted. Thus, for example, when the surgical tool 1 is attached within a curved path, as in an insertion unit of a flexible endoscope or when the surgical tool 1 is guided along the curved path in the inside of a body, the surgical tool 1 of the present embodiment is easily inserted.

Additionally, since the surgical tool 1 of the present embodiment has the tension-applying section 22 between the first traction member 6 and the second traction member 7, if the pinion 19 is connected to the power source 11, the tension applied by the tension-applying section 22 is not applied to the distal end side (the first traction member 6 and the second traction member 7). For this reason, controllability does not deteriorate easily, applying suitable tension.

Modification Example 1-1

Figure 4:
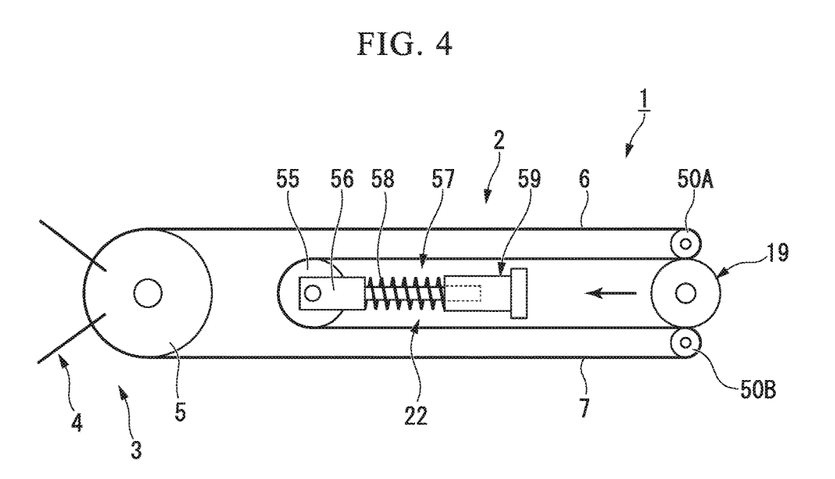
FIG. 4 is a schematic view illustrating the configuration of a modification example of the embodiment.
Figure 5:
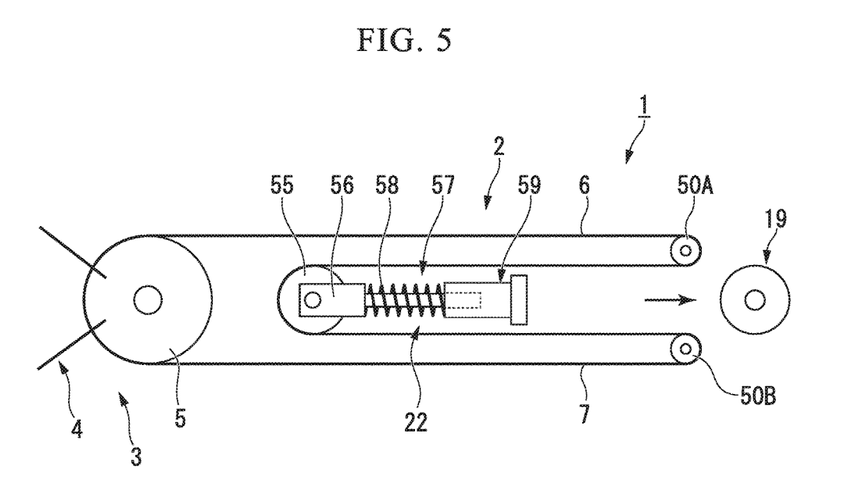
FIG. 5 is a schematic view illustrating the configuration of the modification example.

Next, a modification example of the above embodiment will be described. FIGS. 4 and 5 are schematic views illustrating the configuration of the present modification example.

As illustrated in FIGS. 4 and 5, the present modification example has a pair of pulleys 50A and 50B having rotating shafts parallel to each other and having teeth meshing with the pinion 19 formed in outer peripheral surfaces thereof, instead of the first internal gear 50 and the second internal gear 51.

Grooves that a series of linear members serving as the first traction member 6 and the second traction member 7 enter are formed in portions of the outer peripheral surfaces of the pair of pulleys having the teeth formed.

In the present modification example, as the pinion 19 meshes with both of the pair of pulleys 50A and 50B or the pinion 19 is separated from both of the pair of pulleys 50A and 50B, the same effects as those of the above embodiment are exhibited. In addition, the movement direction of the pinion 19 with respect to the pair of pulleys 50A and 50B is not particularly limited. For example, the pinion 19 may move in the direction of a rotational axis of the pair of pulleys 50A and 50B. Additionally, the position of the pinion 19 may not change and the air of pulleys 50A and 50B may move with respect to the pinion 19.

Modification Example 1-2

Figure 6:
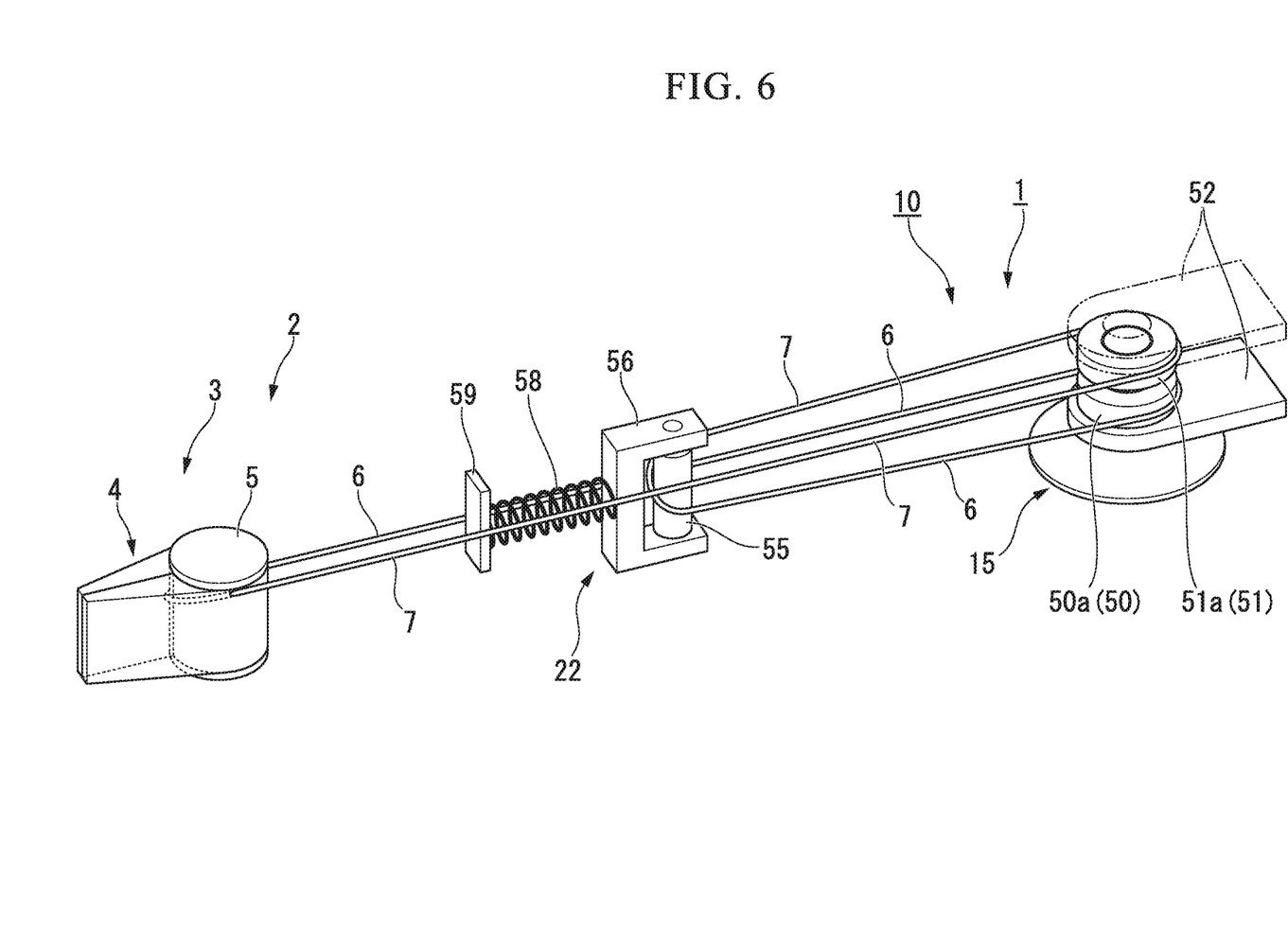
FIG. 6 is a perspective view illustrating the internal structure of a surgical tool of another modification example of the embodiment.

Next, another modification example of the above embodiment will be described. FIG. 6 is a perspective view illustrating the internal structure of a surgical tool of the present modification example.

In the present modification example, the orientation of the tension-applying section 22 is opposite to the orientation of the surgical tool 1 of the above embodiment. That is, in the above embodiment, the spring 58 functions as a push spring, and thereby, has a function to apply tension. However, in the present modification example, the spring 58 functions as a pull spring and thereby has a function to apply tension.

Even in such a configuration, the same effects as those of the surgical tool 1 of the above embodiment are exhibited.

In addition, in the present modification example, although the guide 57 may be provided, the guide 57 may not be provided. Since the spring 58 tends to pass along the shortest distance from a fixed end even in a case where the guide 57 is not provided, the same linear motion as in a case where the guide 57 is provided is possible. Since any influence exerted by the sliding in the guide 57 is not received when the guide 57 is not provided, tension can be efficiently applied to the first traction member 6 and the second traction member 7. Moreover, the tension-applying section 22 can be arranged compactly since the guide 57 is not provided.

Second Embodiment

Figure 7:
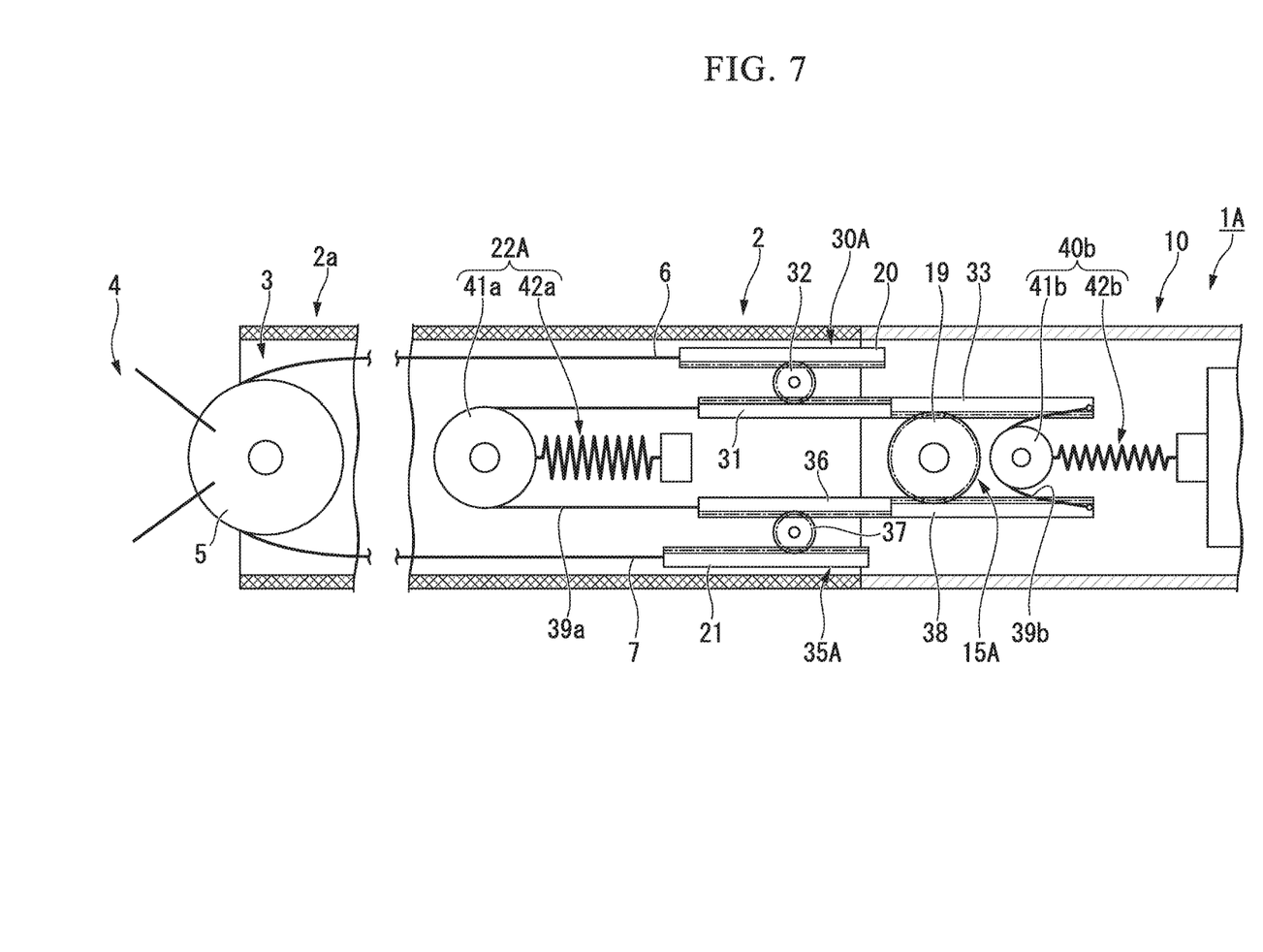
FIG. 7 is a schematic view illustrating a surgical tool of a second embodiment of the invention.
Figure 8:
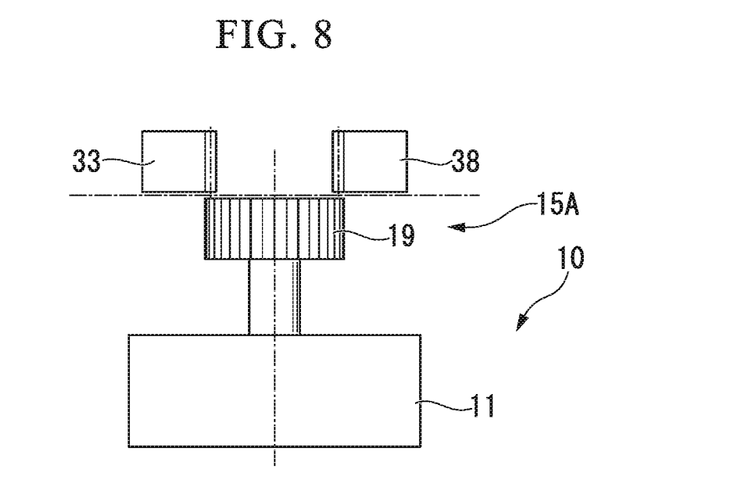
FIG. 8 is a schematic view illustrating a portion of the driving unit in the surgical tool of the embodiment.
Figure 9:
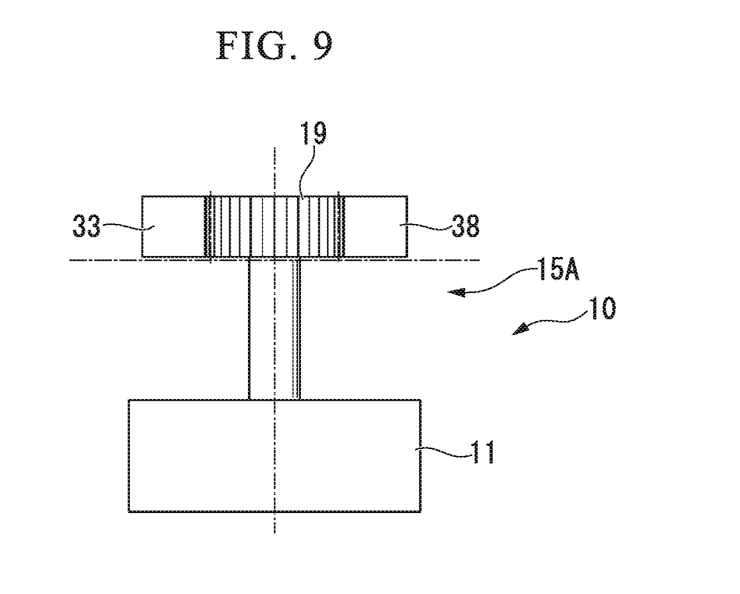
FIG. 9 is a schematic view illustrating a portion of the driving unit.

Next, a second embodiment of the invention will be described. FIG. 7 is a schematic view illustrating a surgical tool of the present embodiment. FIGS. 8 and 9 are schematic views illustrating a portion of the driving unit in the surgical tool.

A surgical tool 1A of the present embodiment illustrated in FIG. 7 is attachable to and detachable from the insertion unit 2 and the driving unit 10, similar to the first embodiment.

The surgical tool 1A of the present embodiment has a switching section 15A having a different configuration, instead of the switching section 15 described in the first embodiment.

The switching section 15A has a first rack part 30A and a second rack part 35A.

The first rack part 30A has a first traction rack 20 to which the first traction member 6 is fixed, a first facing rack 31 that has teeth facing the teeth of the first traction rack 20 and is disposed parallel to the first traction rack 20, a first gear 32 that meshes with both of the first traction rack 20 and the first facing rack 31 so as to connect the first traction rack 20 and the first facing rack 31, and a first pressing rack 33 that is meshable with the pinion 19 described in the first embodiment and is movable forward and backward by the pinion 19 in a longitudinal direction of the first facing rack 31.

The first pressing rack 33 is adapted such that a distal end of the first pressing rack 33 abuts against a proximal end of the first facing rack 31 with the biasing force of a spring part 40b. The first pressing rack 33 does not need to be fixed to the first facing rack 31. That is, in the present embodiment, the uncoupling between the insertion unit 2 and the driving unit 10 is achieved by the first pressing rack 33 and the first facing rack 31 being separable from each other.

The first gear 32 always connects the first traction rack 20 and the first facing rack 31, and the movement direction of the first traction rack 20 is opposite to the movement direction of the first facing rack 31 by the first gear 32.

The second rack part 35A has a second traction rack 21 to which the second traction member 7 is fixed, a second facing rack 36 that has teeth facing the teeth of the second traction rack 21 and is disposed parallel to the second traction rack 21, a second gear 37 that meshes with both of the second traction rack 21 and the second facing rack 36 so as to connect the second traction rack 21 and the second facing rack 36, and a second pressing rack 38 that is meshable with the pinion 19 described in the first embodiment and is movable forward and backward by the pinion 19 in a longitudinal direction of the second facing rack 36.

The second pressing rack 38 is adapted such that a distal end of the second pressing rack 38 abuts against a proximal end of the second facing rack 36 with the biasing force of the spring part 40b. The second pressing rack 38 does not need to be fixed to the second facing rack 36. That is, in the present embodiment, the uncoupling between the insertion unit 2 and the driving unit 10 is achieved by the second pressing rack 38 and the second facing rack 36 being separable from each other.

The second gear 37 always connects the second traction rack 21 and the second facing rack 36, and the movement direction of the second traction rack 21 is always opposite to the movement direction of the second facing rack 36 by the second gear 37.

Additionally, the surgical tool 1A of the present embodiment is provided with a tension-applying section 22A that is connected to the first facing rack 31 and the second facing rack 36. The tension-applying section 22A has a coupling wire 39a that couples the first facing rack 31 and the second facing rack 36, a pulley 41a on which the coupling wire 39a is hung, and a spring 42a that presses the pulley 41a to the distal side.

The tension-applying section 22A in the present embodiment applies suitable initial tension to the first traction member 6 and the second traction member 7 via the first traction rack 20 and the second traction rack 21 by means of the biasing force of the spring 42a.

Moreover, the present embodiment includes a coupling wire 39b that couples the first pressing rack 33 and the second pressing rack 38, and the spring part 40b that presses the coupling wire 39b to the distal side. That is, in the present modification example, the spring part 40b functions to move the first pressing rack 33 and the second pressing rack 38 to the distal side. The spring part 40b has a pulley 41b and a compression spring 42b.

When the insertion unit 2 and the driving unit 10 of the surgical tool 1A are uncoupled, the first pressing rack 33 is separated from the first facing rack 31 and the second pressing rack 38 is separated from the second facing rack 36. Thus, when the pinion 19 does not mesh with the first pressing rack 33 and the second pressing rack 38, both the first pressing rack 33 and the second pressing rack 38 are at positions where the first and second pressing racks are moved to the distal side by a biasing force transmitted to the first pressing rack 33 and the second pressing rack 38 from the spring part 40b.

When the insertion unit 2 and the driving unit 10 of the surgical tool 1A are attached and the pinion 19 does not mesh with the first pressing rack 33 and the second pressing rack 38, the spring part 40b presses the first pressing rack 33 against the proximal end of the first facing rack 31 and presses the second pressing rack 38 against the proximal end of the second facing rack 36.

Next, the operation of the surgical tool 1A of the present embodiment will be described.

In the present embodiment, in a situation in which the insertion unit 2 has a curved shape as in the first embodiment, such as when the treatment section 3 is guided to an object region to be treated, tension applied the first traction member 6 and the second traction member 7 can be maintained at a predetermined initial tension. That is, in the present embodiment, as illustrated in FIG. 8, a predetermined initial tension is applied to the first traction member 6 and the second traction member 7 by separating the pinion 19 from the first pressing rack 33 and the second pressing rack 38. In the present embodiment, the first pressing rack 33 and the second pressing rack 38 are manually attachable to and detachable from the pinion 19 in the work of attaching and detaching the insertion unit 2 and the driving unit 10. In addition, the first pressing rack 33 and the second pressing rack 38 may be attachable to and detachable from the pinion 19 by electric operation. In this case, the first pressing rack 33 and the second pressing rack 38, and the pinion 19 are moved relative to each other by, for example, an electric actuator.

As illustrated in FIG. 9, as the pinion 19 meshes with the first pressing rack 33 and the second pressing rack 38, the treatment section 3 is operable.

As illustrated in FIG. 7, in the surgical tool 1A of the present embodiment, if the first pressing rack 33 presses the proximal end of the first facing rack 31, the first pressing rack 33 moves the first facing rack 31 to the distal side. Moreover, the first facing rack 31 rotates the first gear 32, and the first gear 32 moves the first traction rack 20 that is fixed to the first traction member 6 to the proximal side. Accordingly, in the surgical tool 1A of the present embodiment, if the first pressing rack 33 is moved to the distal side, the first traction member 6 is tractioned to the proximal side.

In a process in which the first pressing rack 33 moves to the distal side, the second pressing rack 38 also meshes with the pinion 19. The power transmitted from the pinion 19 to the second pressing rack 38 becomes power that moves the second traction member 7 to the distal side. On the contrary, in a process in which the second pressing rack 38 moves to the distal side, the first pressing rack 33 also meshes with the pinion 19. The power transmitted from the pinion 19 to the first pressing rack 33 becomes power that moves the first traction member 6 to the distal side. However, since the pinion 19 is first separated from the first pressing rack 33 and the second pressing rack 38 and the magnitude of the initial tension is adjusted, loosening or tightening of the first traction member 6 and the second traction member 7 does not easily occur.

Additionally, if the second pressing rack 38 illustrated in FIG. 7 presses the proximal end of the second facing rack 36, the second pressing rack 38 moves the second facing rack 36 to the distal side. Moreover, the second facing rack 36 rotates the second gear 37, and the second gear 37 moves the second traction rack 21 that is fixed to the second traction member 7 to the proximal side. Accordingly, in the surgical tool 1A of the present embodiment, if the second pressing rack 38 is moved to the distal side, the second traction member 7 is tractioned to the proximal side.

In this way, the surgical tool 1A of the present embodiment, similar to the first embodiment, is a compact surgical tool that can keep initial tension constant as compared to the related-art structure in which a power source, a clutch, or the like is frequently used in order to adjust tension.

Modification Example

Figure 10:
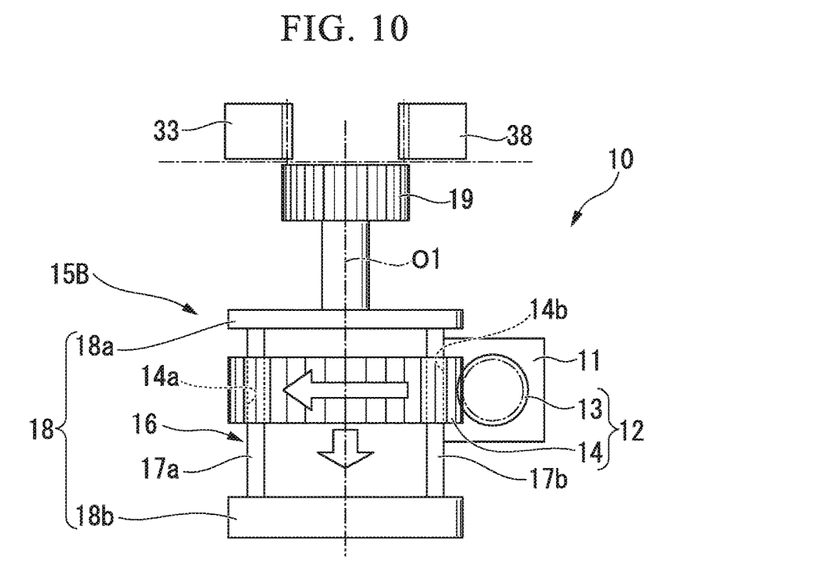
FIG. 10 is a schematic view illustrating the configuration of a modification example of the embodiment.
Figure 11:
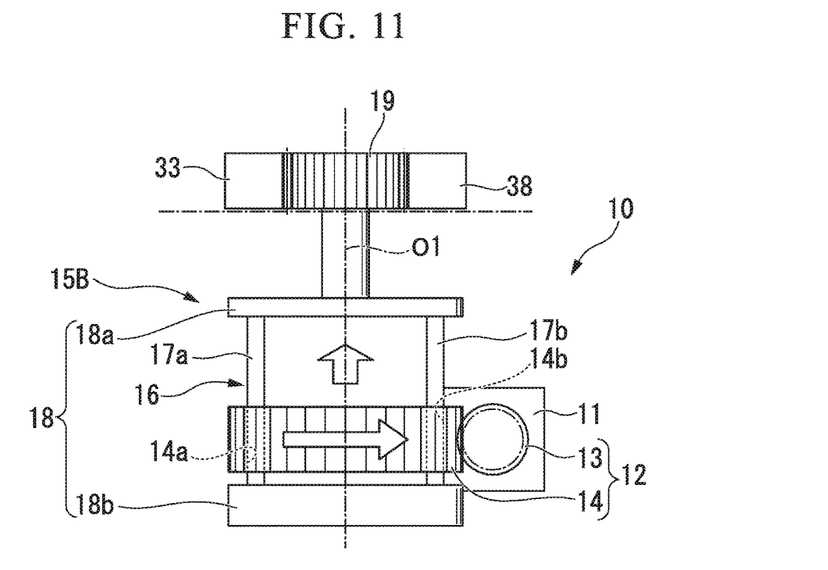
FIG. 11 is a schematic view illustrating the configuration of the modification example.

Next, a modification example of the above second embodiment will be described. FIGS. 10 and 11 are schematic views illustrating a portion of a driving unit in a surgical tool of the present modification example.

The present modification example is different from the above second embodiment in that the present modification example has means for automatically switching a state in which the power output from the power source 11 is transmitted to the first traction member 6 and the second traction member 7.

As illustrated in FIGS. 10 and 11, the driving unit 10 has the power source 11 that generates power for swinging the treatment section 3 illustrated in FIG. 1, a transmission part 12 that is connected to the power source 11, and a switching section 15B that is connected to the transmission part 12.

The power source 11 receives a driving signal generated on the basis of operation input using the master arms 500a and 500b illustrated in FIG. 1, and generates power corresponding to operation input to master arms 500a and 500b. The configuration of the power source 11 is not particularly limited. In the present modification example, the power source 11 is, for example, a servo motor.

The transmission part 12 has a worm gear 13 that is fixed to an output shaft of a servo motor serving as the power source 11, and a worm wheel 14 that meshes with the worm gear 13.

The worm gear 13 and the worm wheel 14 always mesh with each other, and the worm wheel 14 is held by holding means (not illustrated) so that a rotation center O1 of the worm wheel 14 (to be described below) passes through a gap between the first pressing rack 33 and the second pressing rack 38. Additionally, two through-holes 14a and 14b through which two coupling shafts 17a and 17b (to be described below) are inserted through freely so as to be movable forward and backward are formed in the worm wheel 14 so as to extend in the direction of the rotation center of the worm wheel 14.

The respective centers of the above two through-holes 14a and 14b formed in the worm wheel 14 are arranged at positions separated from each other by an equal distance with the rotation center of the worm wheel 14 interposed therebetween, and are arranged parallel to a straight line passing through the rotation center of the worm wheel 14 when viewed from a direction in which the rotation center of the worm wheel 14 extends. In addition, as long as the respective centers of the above two through-holes 14a and 14b correspond to the positions of the coupling shafts 17a and 17b, these centers may not be separated from each other by an equal distance with the rotation center of the worm wheel 14 interposed therebetween.

The switching section 15B has a movable part 16 that is movable forward and backward in the direction in which the rotation center of a worm wheel 14 extends and that is integrally rotatable with the worm wheel 14, the pinion 19 that is fixed to the movable part 16 and is coaxial with the rotation center of the worm wheel 14, a first movable body (the first traction rack 20, the first facing rack 31, and the first pressing rack 33, refer to FIG. 7) that is fixed to the first traction member 6, and a second movable body (the second traction rack 21, the second facing rack 36, and the second pressing rack 38, refer to FIG. 7) that is fixed to the second traction member 7.

The movable part 16 has the two coupling shafts 17a and 17b that are respectively inserted through the through-holes 14a and 14b of the worm wheel 14 and extend parallel to the rotation center of the worm wheel 14, and end members 18 (a first end member 18a and a second end member 18b) that are provided at both ends of the respective coupling shafts 17a and 17b so as to couple the respective coupling shafts 17a and 17b.

The two coupling shafts 17a and 17b are arranged at positions separated from each other by an equal distance with the rotation center of the worm wheel 14 interposed therebetween, and are arranged parallel to a straight line passing through the rotation center of the worm wheel 14 when viewed from the direction in which the rotation center of the worm wheel 14 extends.

It is preferable in terms of design and assembly that the respective coupling shafts 17a and 17b are inserted into the respective through-holes 14a and 14b that are present at the positions apart from each other by an equal distance with the rotation center of the worm wheel 14 interposed therebetween.

In addition, instead of the coupling shafts 17a and 17b being provided, another structure in which the first end member 18a and the second end member 18b are coupled may be adopted. For example, instead of the coupling shafts 17a and 17b, the first end member 18a and the second end member 18b may be coupled together by one coupling shaft. Additionally, the sectional shape of the coupling shafts 17a and 17b in a section orthogonal to the rotation center of the worm wheel 14 is not particularly limited.

The pinion 19 is fixed to any one (the first end member 18a in the present modification example) of the first end member 18a and the second end member 18b. An actuator for moving the movable part 16 in the direction of the rotation center of the worm wheel 14 is coupled to the other (the second end member 18b in the present modification example) of the first end member 18a and the second end member 18b.

The configuration of the second end member 18b and the actuator coupled to the second end member is not particularly limited if the second end member 18b is rotatable with the rotation center of the worm wheel 14 as a center and the second end member 18b is movable forward and backward in the direction of the rotation center of the worm wheel 14.

In the present modification example, the pinion 19 is fixed to the first end member 18a of the movable part 16.

Additionally, the pinion 19 of the present modification example is a spur gear. In addition, tapers for smoothing coupling to the first pressing rack 33 and the second pressing rack 38 may be formed in teeth formed in the pinion 19. Additionally, the pinion 19 and the worm wheel 14 rotate with the same rotation center O1 as a center.

Next, the operation of the surgical tool 1 of the present modification example will be described.

The surgical tool 1 of the present modification example is fixed to a slave arm illustrated in FIG. 1, and the power source 11 of the driving unit 10 operates according to operation input to a master arm. When the first traction member 6 is tractioned in the surgical tool 1, the actuator that moves the second end member 18b of the movable part 16 operates before the power source 11 that rotates the worm wheel 14 of the movable part 16 operates. That is, the actuator (not illustrated) that moves the second end member 18b moves the pinion 19 along the direction of the rotation center thereof up to a position where the teeth of the pinion 19 mesh with the respective teeth of the first pressing rack 33 and the second pressing rack 38. Thereafter, as the power source 11 that rotates the worm wheel 14 of the movable part 16 operates, the first pressing rack 33 and the second pressing rack 38 linearly move in mutually opposite directions.

Even in such a configuration, the same effects as the surgical tool of the above second embodiment are exhibited. Additionally, in the present modification example, the transmission of power from the power source 11 to the first traction member 6 and the second traction member 7 can be controlled independently from the attachment and detachment of the insertion unit 2 and the driving unit 10.

While the preferred embodiments and their modification examples of the invention have been described and illustrated above, it should be understood that these are exemplary of the invention and is not to be considered as limiting. Additions, omissions, substitutions, and other modifications of components can be made without departing from the concept of the invention.

For example, the tapers of the pinion illustrated in the above modification example may be provided in order to smooth the coupling between the pinion and the internal gear even when the pinion and the internal gear mesh with each other. Additionally, tapers for smoothing coupling to the pinion may also be provided in respective teeth of the racks or the internal gear.

Additionally, in the above first embodiment (including the modification examples), a configuration in which the pinion 19 connected to the turning shaft of the power source 11, and the first and second internal gears 50 and 51 attachable to and detachable from the pinion 19 are provided as the switching section 15 and the pinion 19 is meshable with the first and second internal gears 50 and 51 has been described as an example. However, the invention is not limited to this, and for example, a mechanism using a clutch may be adopted.

Figure 12:
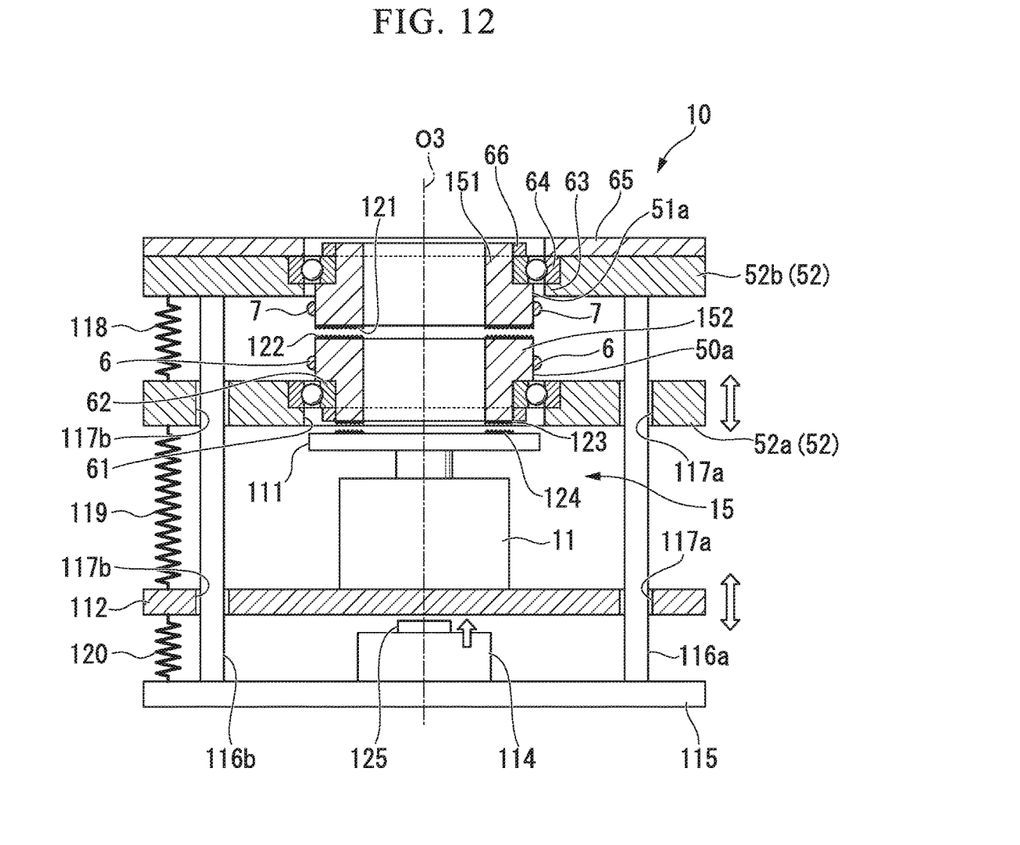
FIG. 12 is a view for describing an example of a design change in the surgical tool of the first embodiment of the invention.

A configuration example of the above clutch mechanism is illustrated below with reference to FIG. 12.

In the present configuration example, instead of the first and second internal gears 50 and 51 disposed at a predetermined interval in the direction of the rotational axis, first and second pulleys 151 and 152 are provided.

Moreover, in the present configuration example, instead of the pinion 19 connected to the turning shaft of the power source 11, for example, a plate-like power transmission part 111 is provided that moves the second pulley 152 to the first pulley 151 side and transmits the power from the power source 11 to the first and second pulleys 151 and 152.

The power source 11 is fixed on the surface of the plate-like third support part 112 directed to the first and second pulleys 151 and 152 side. An electromagnetic clutch 114 capable of abutting against the third support part 112 is arranged opposite to the power source 11 with the third support part 112 interposed therebetween in order to move the power source 11. The electromagnetic clutch 114 is supported, for example, by a fourth support part 115 fixed to a housing (not illustrated).

The fourth support part is coupled to the second support part 63 by coupling rods 116a and 116b. The coupling rods 116a and 116b are inserted through through-holes 117a and 117b formed in the first support part 61 and the third support part 112. The coupling rods 116a and 116b guide the movement of the first support part 61 and the third support part 112 in the direction of the rotational axis, and do not move in a rotational direction. In addition, the number, positions, and cross-sectional shape of coupling rods are not particularly limited if the third support part 112 is capable of being guided and moved in the direction of the rotational axis and the third support part 112 does not move in the rotational direction.

Between the second, first, third, and fourth support parts 63, 61, 112, and 115 which face each other push springs 118, 119, and 120 are provided which have biasing forces in a direction in which the respective facing support parts are separated from each other in the direction of the rotational axis. The respective support parts are coupled together by the push springs 118, 119, and 120. In addition, although the number of push springs between the respective support parts is illustrated as one in FIG. 12, the number of push springs is not limited to one.

Facing surfaces of the first pulley 151 and the second pulley 152, and facing surfaces of the second pulley 152 and the power transmission part 111 are provided with meshing parts 121, 122, 123, and 124 that mesh with each other when the power transmission part 111 and the second pulley 152 move to the first pulley 151 side.

The electromagnetic clutch 114 is provided with a forward/backward movable part 125 that is movable forward and backward in the direction of the rotational axis by performing energization and non-energization.

Next, in the above clutch mechanism, the operation of performing switching between a state in which the power can be transmitted from the power source 11 to the first and second traction members 6 and 7 and a state in which the power cannot be transmitted will be described.

By energizing the electromagnetic clutch 114, the forward/backward movable part 125 moves forward toward the second support part 63 side in the direction of the rotational axis.

The third support part 112 moves to the second support part 63 side against the biasing force of the push spring 119 through the above forward movement of the forward/backward movable part 125, the power transmission part 111 moves to the second pulley 152 side together with the power source 11 through the movement of the third support part 112, and the meshing part 123 of the second pulley 152 meshes with the meshing part 124 of the power transmission part 111.

After the meshing between the meshing part 123 and the meshing part 124, the second pulley 152 further moves to the first pulley 151 side against the biasing force of the push spring 118, and the meshing part 121 of the first pulley 151 and the meshing part 122 of the second pulley 152 mesh with each other.

By bringing about a state in which the power transmission part 111, the second pulley 152, and the first pulley 151 mesh with each other as described above, a state in which the power from the power source 11 can be transmitted to the second traction members 6 and 7 is brought about. By energizing the power source 11 in a state in which the power from the power source 11 can be transmitted to the first and second traction members 6 and 7, the power of rotation when the power source 11 rotates is transmitted to the first and second traction members 6 and 7 via the power transmission part 111 and the first and second pulleys 151 and 152.

In this case, since the first support part 61 and the third support part 112 are not rotated by the coupling rods 116a and 116b, the power transmission part 111 and the first and second pulleys 151 and 152 rotate with respect to the gear case 52.

Additionally, by non-energizing the electromagnetic clutch 114, the forward/backward movable part 125 moves backward from the third support part 112.

As the forward/backward movable part 125 moves backward from the third support part 112, the respective facing support parts are separated from each other by the biasing forces of the respective push springs 118, 119, and 120. As the respective facing support parts are separated from each other, the power transmission part 111, the second pulley 152, and the first pulley 151 are separated from each other, and are brought into a non-meshing state from a meshing state. Along with this, a state in which the power from the power source 11 cannot be transmitted to the first and second traction members 6 and 7 is brought about.

In addition, although the non-energization of the power source 11 may be performed at any time among when the above non-meshing state is brought about, simultaneously with the non-energization of the electromagnetic clutch 114, and before the non-energization of the electromagnetic clutch 114, it is preferable to perform this non-energization before the non-energization of the electromagnetic clutch 114.

Additionally, the clutch mechanism is not limited to the above configuration, but the electromagnetic clutch may be constituted of the power source 11 and the power transmission part 111 without disposing the electromagnetic clutch 114 on the lower side (in FIG. 12) of the third support part 112 by which the power source 11 is supported.

First, for example, the third support part 112 is fixed to the housing, and the coupling rods 116a and 116b are coupled to the third support part 112.

For example, by energizing or non-energizing the power source 11, the power transmission part 111 moves forward and backward in the direction of the rotational axis. In addition, the rotation and forward and backward movement of the power transmission part 111 are appropriately controlled for switching or the like by, for example, a control unit that is provided outside.

A pull spring is disposed between the power transmission part 111 and the power source 11, so that the power transmission part 111 is moved back from the second pulley 152 with the spring force of the pull spring at the time of non-energization with a predetermined interval in the direction of the rotational axis. For this reason, the push spring 119 may not be particularly provided.

By energizing the power source 11, the power transmission part 111 is moved forward toward the second pulley 152 side (second support part 63 side) in the direction of the rotational axis against the spring force of the pull spring.

Since a switching operation using this mechanism is the same as that of the above embodiment, the description thereof is omitted.

Additionally, the constituent elements illustrated in the above-described respective embodiments and respective modification examples can be appropriately combined together.

What is claimed is:

1. A surgical tool comprising:
 a treatment section that treats an object to be treated;
 a power source that generates a power to operate the treatment section;
 a traction section connected to the treatment section and the power source;
 a switching section that switches a transmission state of the power from the power source to the traction section between a state in which the power can be transmitted and a state in which the power cannot be transmitted; and
 a tension-applying section that has a pulley and applies a predetermined initial tension to the traction section by applying a power to the pulley in the state in which the power cannot be transmitted,
 wherein the traction section is hung on the pulley via the power source from the treatment section and is connected to the treatment section via the power source.

2. The surgical tool according to claim 1, wherein the traction section is slidably hung on the pulley.

3. The surgical tool according to claim 1, wherein the switching section includes:
 a driver connected to the power source; and
 a movable body that is connected to the traction section, is attachable to and detachable from the driver, and is engaged with the driver and thereby moved by the driver.

4. The surgical tool according to claim 3, wherein
 the driver is a pinion connected to the power source, and
 the movable body is an internal gear having an outer peripheral surface frictionally engageable with the traction section and an inner peripheral surface having gear teeth meshing with the pinion and is attachable to and detachable from the pinion.

5. The surgical tool according to claim 3, wherein
 the driver is a pinion connected to the power source,
 the movable body is a rack coupled to the traction section, and
 the switching section further includes a movable part that moves the pinion with respect to the rack in order to attach and detach the pinion to and from the rack.

6. A surgical tool comprising:
 an end effector configured to be moved by a driving force to perform a treatment;
 an actuator configured to generate the driving force to move the end effector to perform the treatment;
 a wire configured to transmit the driving force generated by the actuator to the end effector;
 one or more movable bodies configured to switch between a transmission state in which the one or more movable bodies engage the actuator to transmit the driving force to the wire and a non-transmission state in which the one or more movable bodies disengage from the actuator so that the driving force generated by the actuator is not transmitted to the wire; and
 a biasing member configured to apply a predetermined initial tension to the wire by applying a biasing force to a pulley in the non-transmission state.

7. The surgical tool according to claim 6, wherein the wire is slidably hung on the pulley.

8. The surgical tool according to claim 6, further comprising a pinion coupled to the actuator,
 wherein the one or more movable bodies are attachable to and detachable from the pinion.

9. The surgical tool according to claim 8,
 wherein the one or more movable bodies comprise an internal gear comprising:
 an outer peripheral surface frictionally engageable with the wire; and
 an inner peripheral surface comprising gear teeth meshing with the pinion.

10. The surgical tool according to claim 8,
 wherein the one or more movable bodies comprise a rack coupled to the wire, and the one or more movable bodies are configured to move the pinion with respect to the rack.

* * * * *